(12) United States Patent
Meftah et al.

(10) Patent No.: US 8,847,613 B2
(45) Date of Patent: Sep. 30, 2014

(54) CAPACITIVE SENSING SYSTEM

(75) Inventors: Mohammed Meftah, Eindhoven (NL); Bastiaan Feddes, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 226 days.

(21) Appl. No.: 13/320,548

(22) PCT Filed: May 31, 2010

(86) PCT No.: PCT/IB2010/052414
§ 371 (c)(1),
(2), (4) Date: Nov. 15, 2011

(87) PCT Pub. No.: WO2010/140106
PCT Pub. Date: Dec. 9, 2010

(65) Prior Publication Data
US 2012/0062253 A1    Mar. 15, 2012

(30) Foreign Application Priority Data

Jun. 5, 2009 (EP) .................................... 09162001

(51) Int. Cl.
| | |
|---|---|
| *G01R 27/26* | (2006.01) |
| *A61B 5/024* | (2006.01) |
| *A61B 5/00* | (2006.01) |
| *A61B 5/11* | (2006.01) |
| *A61B 5/08* | (2006.01) |
| *A61B 5/113* | (2006.01) |

(52) U.S. Cl.
CPC ........... *A61B 5/1126* (2013.01); *A61B 5/02438* (2013.01); *A61B 5/6804* (2013.01); *A61B 5/6887* (2013.01); *A61B 5/024* (2013.01); *A61B 5/0816* (2013.01); *A61B 5/113* (2013.01)
USPC .......................................... 324/686; 324/658

(58) Field of Classification Search
USPC ............ 324/686, 658, 649, 600, 519; 702/47, 702/52; 340/562, 545.4; 73/718, 724, 780, 73/335.04, 514.32, 862.337, 862.626, 73/304 C
See application file for complete search history.

(56) References Cited

U.S. PATENT DOCUMENTS

| | | | |
|---|---|---|---|
| 4,633,249 A * | 12/1986 | Sasaki ...................... | 340/870.37 |
| 4,696,307 A | 9/1987 | Montgieux | |
| 6,492,911 B1 * | 12/2002 | Netzer ...................... | 340/870.37 |
| 6,807,438 B1 | 10/2004 | Brun Del Re et al. | |

(Continued)

FOREIGN PATENT DOCUMENTS

| | | |
|---|---|---|
| CN | 1969752 A | 5/2007 |
| FR | 2377793 | 8/1978 |

(Continued)

*Primary Examiner* — Hoai-An D Nguyen (57) ABSTRACT

A capacitive sensing system (1) which includes an electrical charge providing unit (4) like an electret foil for providing a permanent electrical charge at a sensing site (6) of the object (3) and a capacitive sensor (2) including a sensing electrode (5) for generating a sensing signal by capacitively sensing the object (3) at the sensing site (6) of the object (3). By providing a permanent electrical charge at the sensing site (6) of the object (3), the bias between the object (3) and the sensing electrode (5) of the capacitive sensor (2) is intentionally preferentially made large, thereby increasing the sensitivity towards mechanical motions. The resulting sensing signal substantially caused by these mechanical motions between the object (3) and the sensing electrode (5) is generally larger than a signal generated substantially by an electrophysiological field.

20 Claims, 5 Drawing Sheets

(56) References Cited

U.S. PATENT DOCUMENTS

| | | |
|---|---|---|
| 7,532,151 B2 * | 5/2009 | Touge et al. ............... 342/27 |
| 7,730,507 B2 * | 6/2010 | Sakai et al. ................ 725/14 |
| 7,898,267 B2 * | 3/2011 | Murari et al. .............. 324/686 |
| 2004/0073104 A1 | 4/2004 | Brun del Re et al. |
| 2006/0030781 A1 | 2/2006 | Shennib |
| 2008/0219464 A1 | 9/2008 | Smith |
| 2010/0043546 A1 * | 2/2010 | Kandori et al. ........... 73/504.12 |
| 2011/0068776 A1 * | 3/2011 | Yokota et al. ............ 324/207.11 |
| 2011/0156943 A1 * | 6/2011 | Wong et al. ............... 341/176 |
| 2012/0061415 A1 * | 3/2012 | Hagleitner ................. 221/1 |
| 2013/0162573 A1 * | 6/2013 | Huang ....................... 345/173 |

FOREIGN PATENT DOCUMENTS

| | | |
|---|---|---|
| GB | 1599373 A | 9/1981 |
| GB | 2129991 A | 5/1984 |
| WO | 9939543 A1 | 8/1999 |
| WO | 03054853 A1 | 7/2003 |
| WO | 2007059692 A1 | 5/2007 |
| WO | 2008152588 A2 | 12/2008 |

\* cited by examiner

CAPACITIVE SENSING SYSTEM

FIELD OF THE INVENTION

The invention relates to a capacitive sensing system and a capacitive sensing method.

BACKGROUND OF THE INVENTION

WO 2008/152588 A1 discloses a capacitive sensor for sensing electrical fields of a body comprising an electrode, a shield, an insulating separation material separating the electrode and the shield and a housing including associated electronic circuits, wherein the tribo-electric property of the insulating separation material or the material used for the housing substantially matches with that of the skin of the body thereby reducing the generation of static charge on the capacitive sensor. The capacitive sensor is used in applications where motions are present during measurement of electrophysiological signals from the body such as electrocardiography or electromyography.

SUMMARY OF THE INVENTION

Even if the generation of static charge on the capacitive sensor is reduced, the sensing signal of the capacitive sensor can still be distorted by the presence of static charges on the body which generally varies over time. Furthermore, the signal can be distorted by motion artifacts due to a varying distance between the object to be sensed and the capacitive sensor. The sensing signal is therefore a small low quality signal.

It is an object of the present invention to provide a capacitive sensing system and a capacitive sensing method, wherein the quality of a sensing signal generated by the capacitive sensing system is improved.

In an aspect of the present invention a capacitive sensing system for sensing an object is presented, wherein the capacitive sensing system comprises:

an electrical charge providing unit for providing a permanent electrical charge at a sensing site of the object, a capacitive sensor comprising a sensing electrode for generating a sensing signal by capacitively sensing the object at the sensing site of the object.

Since the capacitive sensing system comprises an electrical charge providing unit for providing a permanent electrical charge at the sensing site of the object, fluctuations of electrical charge, in particular, of electrical static charge, can be reduced or eliminated, thereby reducing or eliminating a distortion of the sensing signal by these fluctuations, and, thus, improving the quality of the sensing signal generated by the capacitive sensing system. Moreover, by providing a permanent electrical charge at the sensing site of the object, the bias between the object and the sensing electrode of the capacitive sensor is intentionally preferentially made large, thereby increasing the sensitivity towards mechanical motions. The resulting sensing signal substantially caused by these mechanical motions between the object and the sensing electrode is generally larger than a signal generated substantially by an electrophysiological field like ECG or EMG. Thus, a larger signal having a larger signal-to-noise ratio and, therefore, having an improved quality is generated by the capacitive sensing system.

The electrical charge providing unit can be any unit being adapted for providing a permanent electrical charge at the sensing site of the object. Preferred embodiments of the electrical charge providing unit will be described further below.

The permanent electrical charge is preferentially a permanent electrical static charge. An electrical charge is preferentially regarded as being permanent, if the electrical charge is constant in time. A charge is preferentially regarded as being constant in time, if charge variations are smaller than 10%, further preferred smaller than 5% and even further preferred smaller than 3% for at least one minute, further preferred for at least one hour, further preferred for at least one day, further preferred for at least one month, and even further preferred for at least one year.

The capacitive sensing system is preferentially adapted for sensing a body of a person or of an animal, in particular, for generating a physiological signal of the body. The capacitive sensing system can be adapted for sensing the body through cloths, for example, if a person or an animal is located on a chair or in a bed. This allows, for example, monitoring health related parameters while a person is sleeping. The capacitive sensor is preferentially adapted for performing a contact less measurement of mechanical movements of a person or of an animal.

It is preferred that the electrical charge providing unit comprises an electret for being attached to the object for providing the electrical charge.

The electret is preferentially an electret foil. The electrical charge providing unit comprising an electret is an embodiment of the electrical charge providing unit which ensures a reliable and constant over time electrical static charge at the sensing site.

The electret, which is preferentially an electret foil, is preferentially adapted to be attached to a body of a person or of an animal or to other objects that are preferentially mechanically coupled to the body like cloths, chair, bed et cetera.

The electret is a permanently charged material which means that no external biasing is needed and the charge will not disappear over time.

The electret can be adapted to be put on a part of the object, which is preferentially a body, that has to be sensed. The size of the electret, in particular, of the electret foil, can be adapted to the size of the region, which is intended to be sensed, for example, if only a small muscle group has to be sensed, the electret can have a smaller size, and if, for example, the upper chest has to be sensed for probing respiration, the size of the electret can be larger. The electret, in particular, the electret foil, can be adapted to be used as a disposable foil.

It is further preferred that the electrical charge providing unit comprises a voltage source and an electrically conducting element for being attached to the object, wherein the voltage source is connected to the electrically conducting element for providing the permanent electrical charge.

The voltage source is, for example, a battery of several volts, for example, a battery having less than ten volts.

The conducting element is preferentially a conductive foil. Also this conductive foil can be adapted to the size of a region, which is intended to be sensed. Also the conductive foil can be adapted to be used as a disposable foil.

The conductive foil is preferentially made of a bio compatible material. The conductive foil is preferentially adapted to be suitable for being worn longer periods of time, for example, for being worn minutes to days. The conductive foil is preferentially thin, i.e. has preferentially a thickness smaller than 1 mm, in order to be as unobtrusive as possible. The conductive foil can be made of a conductive textile.

A permanent amount of electrical static charge is provided at the sensing site. Therefore, a movement of the sensing site with respect to the sensing electrode, i.e. a movement of the permanent amount of electrical static charge with respect to the sensing electrode, yields a modification of the capacitance of the capacitor formed by the sensing electrode and the object and, thus, a change of the sensing signal, which is mainly caused by this relative movement and not by fluctuating static charges on the object. Thus, by detecting changes of the sensing signal distance variations between the object and the sensing electrode can be determined.

It is preferred that the capacitive sensing system further comprises a property determination unit for determining a property of the object from the generated sensing signal.

Variations of the sensing signal can be related to a movement caused by heart activity, respiration, mechanical activity of muscles and other mechanical vibrations appearing from the object, if the object is a body of a person or of an animal. Also other kinds of movements of the object, in particular, of the body, can be determined from the generated sensing signal. Thus, the property determination unit is preferentially adapted to determine, for example, the heart rate or respiration from the generated sensing signal. However, also other property related to a movement of the object can be determined from the generated sensing signal.

If the variations of the sensing signal relate to mechanical vibrations caused by different effects like heart activity and respiration, these effects can be separated by using frequency filtering techniques for filtering the part of the sensing signal that corresponds to the respective effect.

In a further aspect of the present invention a computer program for sensing an object is presented, wherein the computer program comprises program code for causing a capacitive sensing apparatus to carry out following steps:

generating a sensing signal by capacitively sensing the object at a sensing site of the object, at which a permanent electrical charge is provided by an electrical charge providing unit, by a sensing electrode of a capacitive sensor, determining a property of the object from the generated sensing signal by a property determination unit, when the computer program is run on a computer controlling the capacitive sensing apparatus.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF EMBODIMENTS

Figure 1:
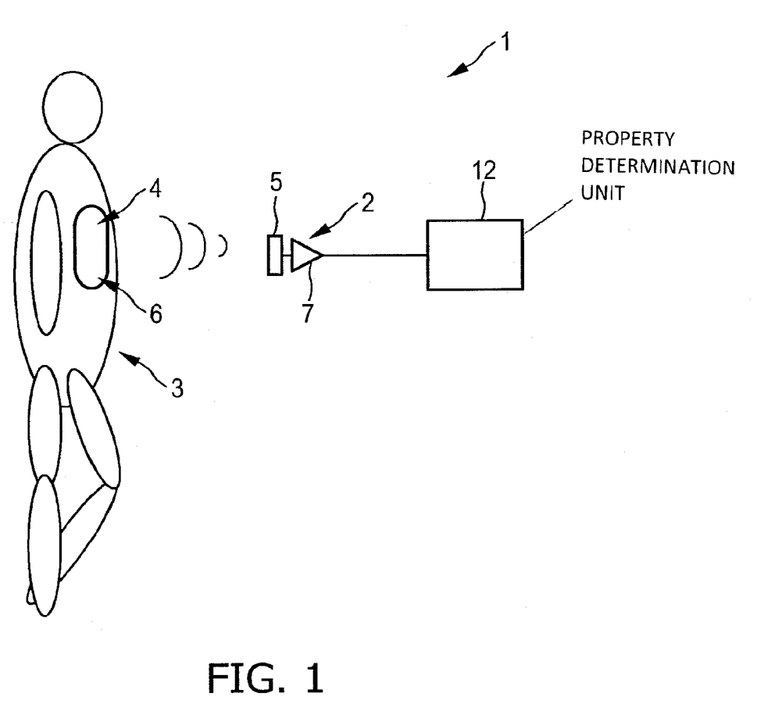
FIG. 1 shows schematically and exemplarily a capacitive sensing system for sensing an object.

FIG. 1 shows schematically and exemplarily an embodiment of a capacitive sensing system for sensing an object. The capacitive sensing system 1 comprises a capacitive sensor 2 and an electrical charge providing unit 4. The capacitive sensor 2 includes a sensing electrode 5 for generating a sensing signal by capacitively sensing the object 3 at a sensing site 6 of the object 3. The electrical charge providing unit 4 is adapted to provide a permanent electrical charge at the sensing site 6 of the object 3.

The capacitive sensing system 1 is adapted for sensing a body of a person or of an animal for determining a physiological property of the body 3. The capacitive sensing system 1 is adapted for sensing the body 3 through cloth, for example, if a person or an animal is located on a chair or in a bed. This allows, for example, monitoring health related parameters while the person is sleeping.

In the embodiment shown in FIG. 1, the electrical charge providing unit 4 is an electret foil. The electret foil 4 is adapted to be attached to a body 3 of a person or of an animal or to other objects that are preferentially coupled to the body like cloth, chair, bed et cetera. The electret foil 4 at the sensing site 6 ensures a reliable and constant over time electrical static charge at the sensing site 6.

The electret foil comprises an attachment mechanism for being attached to the body 3 or to the other objects exemplarily mentioned above that are preferentially mechanical coupled to the body. The attachment mechanism is, for example, an adhesive, a strap or it can be any other means for attaching the electret foil to the body or to the above mentioned other objects that are preferentially coupled to the body.

The electret foil 4 is a permanently charged material which means that no external biasing is needed and the charge will not disappear over time.

The size of the electret foil 4 is adapted to the size of the region, which is intended to be sensed, for example, if only a small muscle group has to be sensed, the electret foil 4 can have a smaller size, and if, for example, the upper chest has to be sensed for probing respiration, the size of the electret foil 4 can be larger.

The capacitive sensor 2 comprises the electrode 5 and electronics 7 which will be exemplarily described further below with reference to FIG. 3.

Since a permanent amount of electrical static charge is provided by the electret foil 4 at the sensing site 6, a movement of the sensing site 6 with respect to the sensing electrode 5, i.e. a movement of the permanent amount of electrical static charge with respect to the sensing electrode 5, yields a modification of the capacitance of the capacitor formed by the sensing electrode 5 and the object 3 with the electret foil 4 and, thus, a change of the sensing signal, which is mainly caused by this relative movement.

The capacitive sensing system 1 further comprises a property determination unit 12 for determining a property of the object 3 from the generated sensing signal, in particularly, from variations of the generated sensing signal.

In this embodiment, the electret foil 4 is coupled to the body 3 at the chest of the person. A movement of the chest of the body 3 is substantially caused by respiration and heart activity. The property determination unit 12 is preferentially adapted to separate variations of the sensing signal caused by heart activity and variations of the sensing signal caused by respiration by using frequency filtering techniques. For example, for retrieving variations of the sensing signal caused by heart activity a frequency filter filtering frequencies between 1 Hz and 30 Hz can be used, and for retrieving variations of the sensing signal caused by respiration frequency filtering techniques can be used which filter frequencies between 0.1 Hz and 1 Hz.

In an embodiment, the property determination unit is adapted to determine the temporal positions of the heart beats and to determine from these temporal positions the heart rate. Alternatively or in addition, the property determination unit can be adapted to determine the respiration rate from the variations of the generated sensing signal, which is preferentially filtered. The temporal positions of the heart beat can, for example, be determined by detecting the temporal positions of the second regions 24 showing large variations of the sensing signal, which are exemplarily shown in FIG. 4 and which will be explained in more detail further below. The respiration rate can, for example, be determined as the frequency of a fundamental oscillation of the sensing signal.

In other embodiments, in addition or alternatively, the property determination unit can be adapted for determining another property of the object from the variations of the sensing signal. For example, the property determination unit can be adapted to determine the mechanical activity of muscles and other mechanical vibrations appearing from the object. The property determination unit can also be adapted to determine other kinds of movements of the object, in particular, a movement of the entire object or of an arm, a leg or the head can be determined from the variations of the sensing signal.

Figure 2:
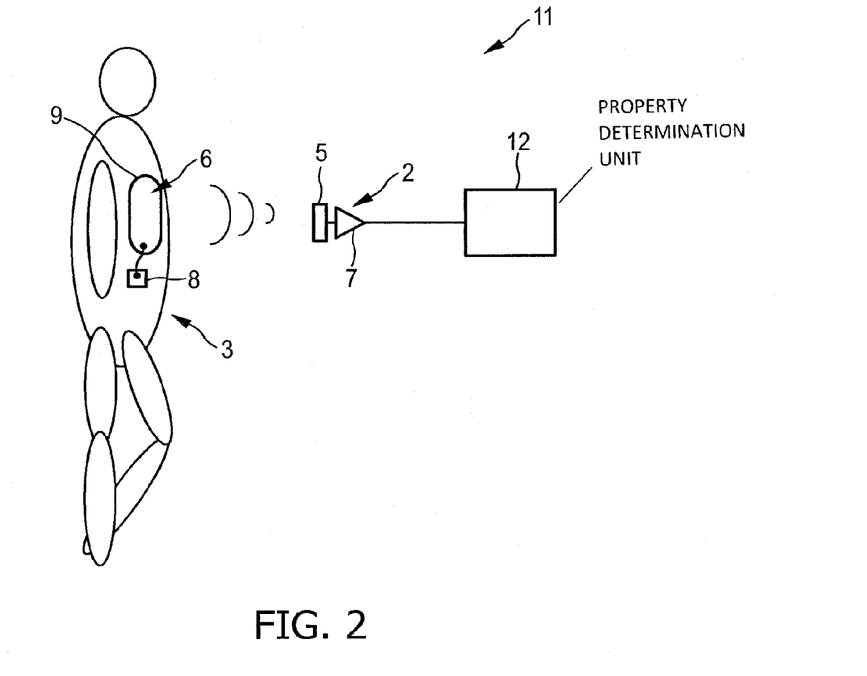
FIG. 2 shows schematically and exemplarily a further capacitive sensing system for sensing an object.

FIG. 2 shows schematically and exemplarily a further embodiment of a capacitive sensing system. The capacitive sensing system 11 shown in FIG. 2 also comprises a capacitive sensor 2 and an electrical charge providing unit. The capacitive sensor 2 comprises a sensing electrode 5 for generating a sensing signal by capacitively sensing the object 3 at a sensing site 6 of the object. The electrical charge providing unit comprises a voltage source 8 and an electrically conducting element 9 for being attached to the object 3, wherein the voltage source 8 is connected to the electrically conducting element 9 for providing a permanent electrical static charge. In this embodiment, the electrically conducting element 9 is a conductive foil. Also this conductive foil 9 is adapted to the size of the region of the object, which is intended to be sensed. In an embodiment, the voltage source 8 is a high voltage generator. In an alternative embodiment, the capacitive sensor, i.e. the probing circuit, is brought to a potential being larger than the potential of the object, which is preferably grounded. Also in this way a permanent electrical charge can be provided at the sensing site of the object, wherein a large permanent bias is provided for generating an amplified sensing signal being indicative of motions between the sensing electrode and the object.

Figure 3:
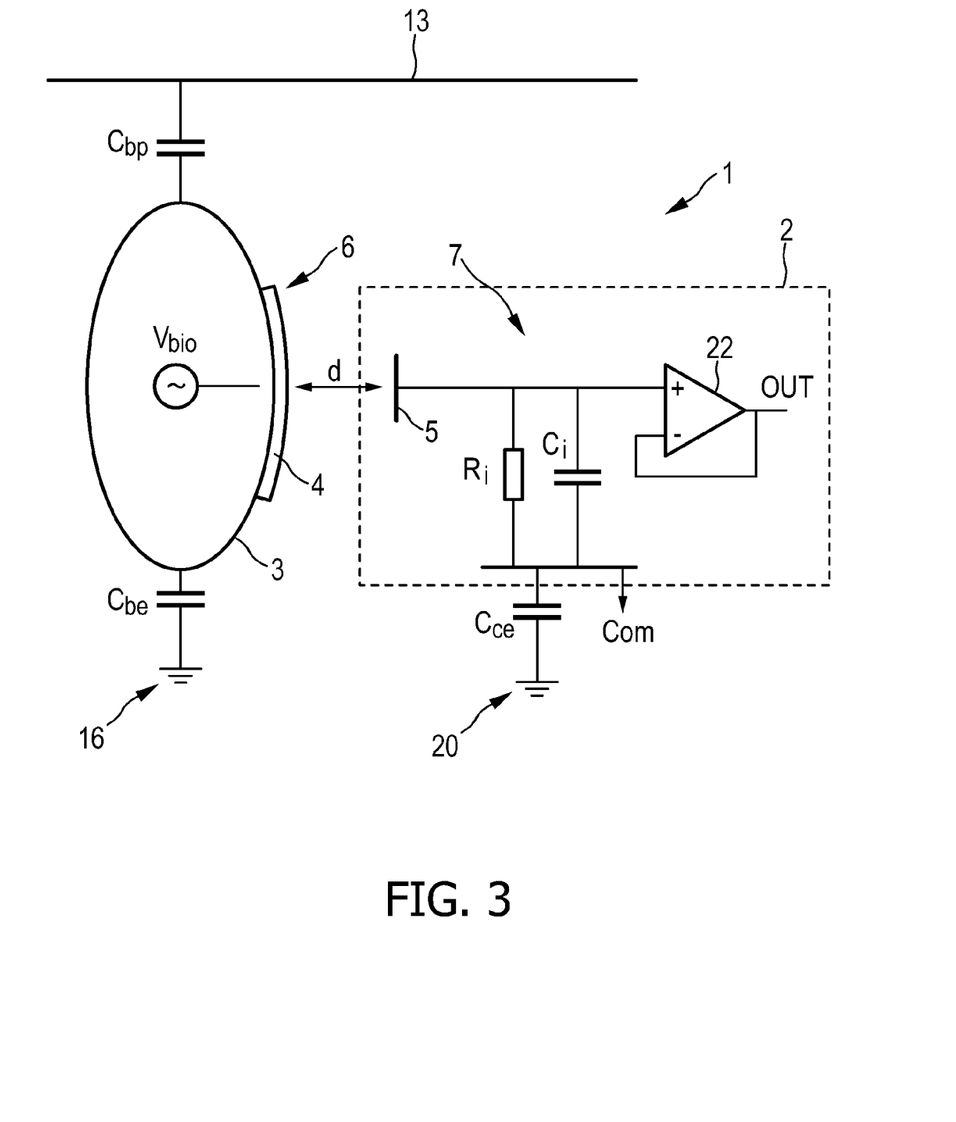
FIG. 3 shows schematically and exemplarily in more detail a circuit of a capacitive sensing system.

FIG. 3 shows schematically and exemplarily an embodiment of the capacitive sensing system, wherein a possible electronic circuit is shown in more detail.

FIG. 3 shows schematically and exemplarily on the left side the body 3 including a source of a bioelectric signal $V_{bio}$ being, for example, an ECG signal. At a reference site 6, which is, for example, a chest of the body 3, a permanent electrical charge is provided by an electret foil 4. The body 3 is capacitively coupled to a power grid 13 with a capacitance $C_{bp}$ and to earth 16 with a capacitance $C_{be}$.

On the right side of FIG. 3 the circuit 7 of the capacitive sensor 2 is schematically and exemplarily shown. The capacitive sensor 2 comprises an electrode 5 that is capacitively coupled to the body 3 over a distance d, a bias resistor $R_i$ and a buffer amplifier 22 with its input capacitance $C_i$. Preferentially, the input capacitance $C_i$ is eliminated using a neutralization technique like the neutralization technique described in U.S. Pat. No. 7,088,175. The capacitive sensor 2 provides an output signal OUT being the sensing signal generated by the capacitive sensor 2. The circuit reference Com is capacitively coupled to earth 20 with capacitance $C_{ce}$ so that the body 3 is also capacitively coupled to the circuit reference via $C_{be}$ and $C_{ce}$.

Figure 4:
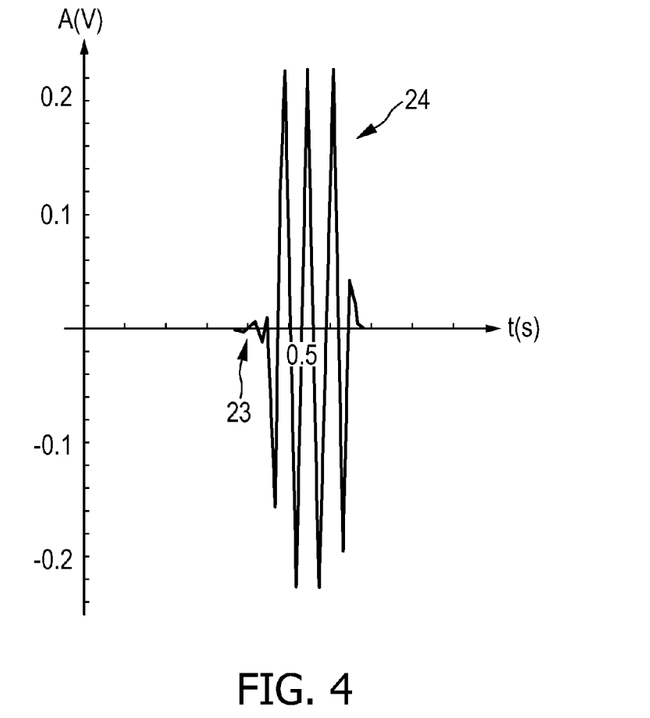
FIG. 4 shows schematically and exemplarily a sensing signal generated by a capacitive sensing system.

A sensing signal generated by the capacitive sensor 2 is schematically and exemplarily shown in FIG. 4. FIG. 4 shows the amplitude A in volts V depending on time t in seconds s. In a first region 23 variations of the sensing signal indicate the ECG signal. The following second region 24 shows much larger variations of the sensing signal caused by movements of the electret foil 4 relative to the electrode 5. Thus, the electret foil 4 yields a strong amplification of the sensing signal. Based on these variations of the sensing signal in the second region 24, the property determination unit 12 can determine a property of the object 3.

The electrical charge providing unit, i.e., for example, the electret foil 4 or the voltage source 8 connected with the electrically conducting element 9, which provide a permanent electrical charge, provides a DC bias between the body 3 and the electrode 5 and amplifies thereby the sensing signal indicative of mechanical motions of the body, i.e. indicative of distance variations between the body and the electrode.

It should be noted that in FIG. 4 it is assumed that the person has held his breath, i.e. respiration movements are neglected in FIG. 4. However, in other embodiments variations of the sensing signal can also be caused by respiration or by other effects. The property determination unit is preferentially adapted to use a frequency filter for filtering the desired effect out of the generated sensing signal and/or the determined distance variations.

The capacitive sensing system can be used for remote sensing of vital body signs like heartbeat, respiration, et cetera. The capacitive sensing system preferentially allows unobtrusively, in particular, through closing, sensing of heartbeat and/or respiration. At least parts of the capacitive sensing system, in particular, the capacitive sensor, is thereby integrated into a bed or a car. The bed is an ideal place for monitoring health related parameters, because sleeping is part of our daily routine. Moreover, a bed is a place where people rest an average of eight hours a day with environmental and physiological conditions that are quite stable, signals therefore can be generated with less motion artifacts.

Figure 5:
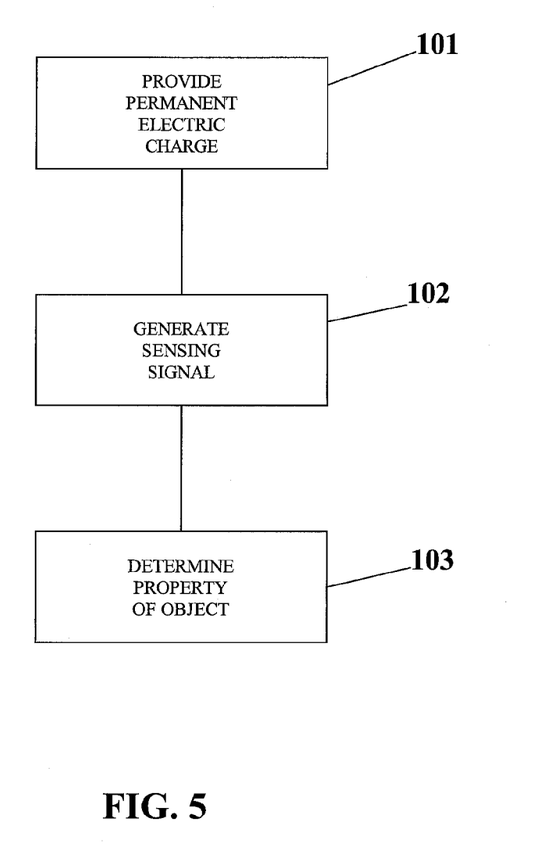
FIG. 5 shows exemplarily a flowchart illustrating a capacitive sensing method for sensing an object.

FIG. 5 shows a flowchart exemplarily illustrating an embodiment of a capacitive sensing method for sensing the object 3.

In step 101, a permanent electrical charge is provided at the sensing site 6 of the object 3 by the electrical charge providing unit, i.e., for example, by attaching the electret foil 4 or the electrically conducting element 9 which is electrically connected to the voltage source 8 to the body 3.

In step 102, a sensing signal is generated by capacitively sensing the object 3 at the sensing site 6 by the sensing electrode 5 of the capacitive sensor 2.

In step 103, the property determination unit 12 determines a property of the object 3 from the generated sensing signal.

In other embodiments, step 103 can be omitted, wherein the capacitive sensing method generates a sensing signal indicative of distance variations between the object and the electrode and, thus, indicative of a movement of the object.

If the voltage source 8 is used together with the conductive foil 9 for providing a permanent electrical static charge on the body 3, the voltage source 8 is preferentially adapted such that a maximum voltage is not exceeded, wherein the maximum voltage is chosen such that the person to which the conductive foil is to be attached, is not adversely affected.

Although in the above described embodiments an electret foil and a voltage source in combination with an electrically conducting foil have been described as an electrical charge providing unit, in other embodiments, other means for providing a permanent electrical charge can be used.

Although in the above described embodiments the permanent electrical static charge is provided on the body of a person for generating a sensing signal indicative of a movement of the chest of the person, in other embodiments movements of other parts of the body of the person or of the entire body of the person can be determined. Furthermore, movements of parts of a body or a the entire body of an animal can be determined. Also movements of other objects like technical objects can be determined by using the capacitive sensing system.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of distance variations or the determination of a property of the object performed by the distance variations determination unit and the property determination unit can be performed by any other number of units or devices, for example, by a single unit only or by more than two units. The determination of the property of the object from the generated sensing signal and/or the control of the capacitive sensing system in accordance with the capacitive sensing method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A capacitive sensing system for sensing physical movement in time varying static charges, the capacitive sensing system comprising:
   an element configured to be mechanically attached to a region of the patient such that the element is subject to carrying the time varying static charges;
   an electrical charge providing unit configured to provide a permanent electrical charge that is constant in time on the element;
   a capacitive sensor comprising a sensing electrode configured to generate a sensing signal by capacitively sensing mechanical movement of the element when the capacitive sensor is placed at a location remote from the element and the patient such that the capacitive sensor performs contact-less measurement of mechanical movements of the patient;
   wherein the permanent electrical charge reduces or eliminates fluctuations in the measurement attributable to the time varying static charges.

2. The capacitive sensing system as defined in claim 1, wherein the element and the electrical charge providing unit includes an electret.

3. The capacitive sensing system as defined in claim 1, wherein the element is electrically conducting and the electrical charge providing unit includes a voltage source electrically connected to the electrically conducting element to provide the permanent electrical charge on the element, wherein the permanent electrical charge is a DC bias between the element and the patient.

4. The capacitive sensing system as defined in claim 1, wherein the capacitive sensor generates a sensing signal indicative of the measurement and further including a property determination unit configured to determine a property of the patient from the generated sensing signal.

5. The capacitive sensing system as defined in claim 4, wherein the property determination unit determines at least one of a respiration rate and a heart rate of the patient.

6. The capacitive sensing system as defined in claim 1, wherein the element includes a permanently charged material which provides the permanent electrical charge which is constant over time.

7. A capacitive sensing method for sensing mechanical movement in an object which carries time varying static charges, the capacitive sensing method comprising the steps of:
   attaching an element which carries an electrical charge that is constant in time at a sensing site of the object such that the element carries the time varying static charges;
   generating a sensing signal by capacitively sensing the mechanical movement in the object using a sensing electrode of a capacitive sensor, that is located remotely from the element, the sensing site, and the object such that the capacitive sensor performs a contact-less measurement of mechanical movements of the object, such that the constant electrical charge reduces distortions in the sensing signal attributable to the time varying static charges.

8. The method as defined in claim 7, further including:
   determining a property of the object from the sensing signal.

9. The method as defined in claim 7, wherein providing the constant electrical charge includes attaching an electret to the object.

10. The method as defined in claim 7, wherein the element is electrically conductive and providing the constant electrical charge includes:
    connecting a DC voltage source across the electrically conducting element and the object to provide the constant electric charge on the electrically conducting element.

11. The method as defined in claim 8, wherein the object is a patient and the determined property includes at least one of heart activity, respiration, and muscle activity.

12. A capacitive sensing system for sensing an object which carries a time varying static charge, the capacitive sensing system comprising:
    one of (1) an electret and (2) a combination electrically conductive element and voltage generator configured to provide a temporally constant static electrical charge, the one of the electret and the electrically conductive element being configured to be mechanically and electrically connected to the object such that the one of the electret and the electrically conductive element mechanically moves with at least a portion of the object and is subject to carrying the time varying static charge; and
    a sensing electrode configured to be disposed remote from the one of the electret and the combination electrically conductive element and the voltage generator, the sensing electrode and the one of the electret and the electrically conductive element contactlessly capacitively coupling such that relative mechanical movement between the one of the electret and the conductive element and the sensing electrode causes changes in a sensing signal output by the sensing electrode, the temporally constant static electrical charge reducing distortions in the sensing signal output attributable to the time varying static charge.

13. The capacitive sensing system as defined in claim 12, wherein the voltage generator is connected across the electrically conductive element and the object.

14. The capacitive sensing system as defined in claim 12, further including:
 a signal analyzer configured to analyze the sensor signal to determine motion of the object.

15. The capacitive sensing system as defined in claim 14, wherein the sensing electrode is configured to be stationarily mounted and the object includes a patient such that the determined motion is indicative of anatomical movement.

16. The capacitive sensing system as defined in claim 12, wherein the object includes a patient and further including:
 a signal analyzer configured to receive the sensing signal from the sensing electrode and to determine an indication of anatomical movement of the patient.

17. The capacitive sensing system as defined in claim 16, wherein the anatomical movement includes at least one of heart rate and respiration.

18. The capacitive sensing system as defined in claim 16, wherein the signal analyzer is configured to determine heart rate and respiration rate.

19. The capacitive sensing system as defined in claim 12, wherein the sensing electrode is mounted to a bed, a car, or a chair.

20. The capacitive sensing system as defined in claim 12, wherein the object includes a patient and wherein the capacitive sensing system is adapted to sense a body of the patient through cloth.

\* \* \* \* \*